United States Patent [19]

Shih et al.

[11] Patent Number: 5,057,313

[45] Date of Patent: * Oct. 15, 1991

[54] DIAGNOSTIC AND THERAPEUTIC ANTIBODY CONJUGATES

[75] Inventors: Lisa B. Shih, Cedar Grove, N.J.; Frederick J. Primus, Potomac, Md.; Milton D. Goldenberg, Short Hills, N.J.

[73] Assignee: The Center for Molecular Medicine and Immunology, Newark, N.J.

[*] Notice: The portion of the term of this patent subsequent to Oct. 13, 2004 has been disclaimed.

[21] Appl. No.: 309,204

[22] PCT Filed: Feb. 25, 1987

[86] PCT No.: PCT/US87/00406

§ 371 Date: Aug. 23, 1988

§ 102(e) Date: Aug. 23, 1988

Related U.S. Application Data

[63] Continuation-in-part of Ser. No. 833,204, Feb. 25, 1986, Pat. No. 4,699,784.

[51] Int. Cl.$^5$ ............... A61K 39/44; A61K 49/02; C07K 17/02; C12N 11/06
[52] U.S. Cl. ................ 424/85.91; 424/85.8; 424/1.1; 424/9; 435/7.9; 435/188; 525/54.1; 530/389; 530/390; 530/391
[58] Field of Search ............ 530/389, 390, 391; 424/85.91, 85.8, 1.1, 9; 435/7, 9, 188

[56] References Cited

U.S. PATENT DOCUMENTS 4,671,958  6/1987  Rodwell et al. ............... 424/85.91
4,699,784 10/1987  Shih et al. .................... 424/85.91

FOREIGN PATENT DOCUMENTS 1079268 6/1980 Canada .
0088695 9/1983 European Pat. Off. .

OTHER PUBLICATIONS

Gilman et al. eds. *Goodman and Gilman's The Pharmacological Basis of Theraputics* 7th ed. MacMillan Pub. Co., N.Y.; pp. 1281–1283 and 1288–1289.
Ghose et al. (1983) Methods Enzymol 93: pp. 280–333.

*Primary Examiner*—Jeffrey E. Russel
*Assistant Examiner*—Kay Kim
*Attorney, Agent, or Firm*—Foley & Lardner

[57] ABSTRACT

The present invention relates to conjugates of diagnostic or therapeutic principles, such as drugs, toxins, chelators, boron compounds and detectable labels, to an antibody, in which the diagnostic or therapeutic principle is first loaded onto a polymer carrier such as an aminodextran or a polypeptide of at least 50 amino acids in length, and this intermediate is in turn site-specifically conjugated to a targeting antibody such as an antitumor antibody. The resultant conjugate substantially retains the immunoreactivity of the antibody, and targets the diagnostic or therapeutic principle to a target tissue or organ where the diagnostic or therapeutic effect is realized.

32 Claims, No Drawings

DIAGNOSTIC AND THERAPEUTIC ANTIBODY CONJUGATES

CROSS REFERENCE TO RELATED APPLICATION

This application is the U.S. national phase application of PCT Application No. PCT/US/00406, filed Feb. 25, 1987, and designating the United States, and is a continuation-in-part of copending application U.S. Ser. No. 833,204, filed Feb. 25, 1986, and now issued as U.S. Pat. No. 4,699,784.

BACKGROUND OF THE INVENTION

The present invention relates to conjugates of diagnostic or therapeutic principles, such as drugs, toxins, chelators, boron compounds and detectable labels, to an antibody, in which the diagnostic or therapeutic principle is first loaded onto a polymer carrier such as an aminodextran or a polypeptide of at least 50 amino acids in length, and this intermediate is in turn site-specifically conjugated to a targeting antibody such as an antitumor antibody. The resultant conjugate targets the diagnostic or therapeutic principle to a target tissue or organ where the diagnostic or therapeutic effect is realized.

Conjugation of cytotoxic drugs to antibodies to achieve a targeted therapeutic result is known. In particular, it is known that methotrexate (MTX) can be conjugated to antibodies and some selective cytotoxicity has been observed. It is desirable to enhance the selectivity and cytotoxicity of such conjugates by increasing the antibody loading of the cytotoxic drug. However, multiple conjugation of individual drug molecules to an antibody eventually reduces its immunoreactivity, the effect being observed when more than about ten drug molecules are loaded.

It has been suggested that the drug be conjugated to an intermediate polymeric carrier, which in turn would be conjugated to antibody. This has the advantage that larger numbers of drug molecules can be attached to the antibody at fewer sites on the antibody itself, so that immunoreactivity is not as seriously compromised.

One approach has been to attach MTX to bovine serum albumin (BSA) and then randomly link the intermediate to antibody, as reported by Garrett et al., Int. J. Cancer, 31:661-670, 1983. These authors were able to attach about 37 MTX molecules to BSA (average molecular weight of 70,000) but the resultant antibody conjugate had an immunoreactivity of only about 28% of that of the intact antibody.

Use of polylysine as a polymer carrier was reported by Ryser et al., Proc. Natl. Acad. Sci. USA, 75:3867-3870, 1978. These authors found that only about 13 MTX per carrier could be loaded and immunoreactivity was poor. In addition, the high amine content of the polymer, largely in the form of charged ammonium groups, caused the conjugate to stick to normal cells and vitiated the selectivity of the cytotoxic effect.

Rowland, U.S. Pat. No. 4,046,722, discloses an antibody conjugate wherein a plurality of molecules of a cytotoxic agent are covalently bound to a polymer carrier of molecular weight 5000-500,000, and the loaded carrier is covalently bound to an antibody by a random attachment to pendant amine or carboxyl groups. The covalent attachment is effected either by direct condensation to form amide bonds between amine groups on one and carboxyl groups on the other component of the conjugate, or by glutaraldehyde linkage of amine groups on the carrier to amine groups on the antibody. Again, this has the disadvantages of loss of immunoreactivity of the antibody and some risk of crosslinking of the antibody and/or the carrier. Ghose et al., J Natl Cancer Inst, 61:657-676, 1978, disclose other antibody-linked cytotoxic agents useful for cancer therapy, but again, covalent attachment is not to the oxidized carbohydrate portion of the antibody. These references show that it is well known in the art to prepare drug-loaded polymer carriers, but that their mode of attachment to antibodies in the past has been random, through pendant amine or carboxyl groups on the antibody.

Chelating groups for radiometals and/or metal ions which can act as magnetic resonance enhancing agents have been covalently bound to antibodies by a variety of methods, most involving random attachment to pendant amine, carboxyl, sulfhydryl, or phenyl groups on the polypeptide chain. Toxins and boron addends have also been linked to antibodies by various methods for targeted therapy, the boron groups being activated by thermal neutron irradiation once they have been localized at the site of a tumor or other pathological lesion by the antibody targeting vehicle to which they are bound. Detectable labels, such as enzymes, DNA segments, fluorescent compounds and the like, have been bound to antibodies for use in assays, again by random coupling to pendant groups.

In an attempt to avoid the undesirable effects of random coupling to antibody and crosslinking, McKearn, et al., in European Patent Application No. 88,695, published on Sept. 14, 1983, disclose a method for preparing antibody conjugates which involves oxidizing the carbohydrate portion of the antibody and linking compounds with free amine groups to the resultant carbonyls (aldehyde and/or ketone groups) by Schiff base formation and optional reductive stabilization. This reference discloses site-specific attachment of a variety of compounds, such as chelators, drugs, toxins, detectable labels and the like, to the oxidized carbohydrate portion of an antibody. Short peptide linkers are disclosed to provide spacers between these compounds and the antibody, either to make the linkage more readily cleaved or resistant to cleavage at the target site. Attachment of the oxidized carbohydrate to a polymer such as an aminodextran is disclosed, but only in the context of linking the antibody to an insoluble support such as a polymer coated bead, plate or tube, such as would be used in an immunoassay. There is no suggestion in this reference to covalently bind a polymer carrier loaded with functional molecules such as drugs, chelators or the like, to the oxidized carbohydrate portion of an antibody to prepare a soluble conjugate for use as a diagnostic or therapeutic agent.

A need therefore continues to exist for an antibody conjugate of a diagnostic or therapeutic principle, such as a drug, toxin, chelator, boron compound or detectable label, that combines high loading with minimal decrease in immunoreactivity for selective targeting of the diagnostic or therapeutic principle to a target tissue or organ, or for highly efficient and sensitive immunoassay or immunohistological applications.

OBJECTS OF THE INVENTION

One object of the present invention is to provide a conjugate of a diagnostic or therapeutic principle to an targeting antibody wherein a plurality of molecules of the diagnostic or therapeutic principle are attached to the antibody, for enhanced diagnostic or therapeutic effect at the target site.

Another object of the invention is to provide a conjugate of a plurality of molecules of a diagnostic or therapeutic principle to an antibody wherein the conjugate has substantially the same immunoreactivity as intact antibody.

Another object of the present invention is to provide a conjugate of an antitumor or antibiotic drug or toxin to an anticancer or antilesion antibody, wherein the conjugate does not appreciably bind to non-target cells or tissues, and wherein the targeted conjugate can enter the tumor cell or site of infection or release its therapeutic principle at the target site, and achieve its tumoricidal or antibiotic effect at the target, while minimizing the systemic side effects of the drug or toxin.

Another object of the invention is to provide an antibody conjugate comprising a plurality of chelators, for use as a targeted imaging agent for scintigraphic or magnetic resonance imaging, or for use as a targeted therapy agent for radioisotope therapy.

Another object of the invention is to provide an antibody conjugate comprising a plurality of boron addends, for use as a neutron activation therapy agent.

Another object of the invention is to provide an antibody conjugate comprising a plurality of detectable labels, for use as a reagent for immunoassay or immunohistology.

Another object of the invention is to provide a method of producing antibody conjugates having the aforementioned properties.

Another object of the present invention is to provide methods of diagnosis and therapy using the foregoing antibody conjugates for targeted delivery of diagnostic and therapeutic principles to sites of lesions and infections, or using the conjugates to carry a plurality of detectable labels for enhanced detection in immunoassay or immunohistological applications.

Upon further study of the specification and appended claims, further objects and advantages of this invention will become apparent to those skilled in the art.

SUMMARY OF THE INVENTION

These objects can be attained by providing an antibody conjugate, comprising a plurality of drug, toxin, chelator, boron addend or detectable label molecules covalently bound to a polymer carrier having at least one remaining free amine group, the loaded carrier in turn being covalently bound through said at least one amino group to the carbohydrate portion of an antibody by a reduced Schiff base linkage.

The invention further includes a method of preparing an antibody conjugate, comprising the steps of:

(a) reacting a polymer carrier to which are covalently bound a plurality of drug, toxin, chelator, boron addend or detectable label molecules, said carrier having at least one remaining free amine group, to an antibody having an oxidized carbohydrate portion; and (b) reductively stabilizing the resultant Schiff base adduct.

Also included in the invention are improved methods of diagnosis and therapy using the antibody conjugates of the invention.

DETAILED DISCUSSION

The general method of preparing an antibody conjugate according to the invention involves reacting an antibody, whose carbohydrate portion has been oxidized, with a carrier polymer loaded with a plurality of drug, toxin, chelator, boron addend or detectable label molecules, and having at least one remaining free amine function. This results in an initial Schiff base (imine) linkage, which is stabilized by reduction to a secondary amine to form the final conjugate.

The carrier polymer is preferably an aminodextran (AD) or a polypeptide (PP) of at least 50 amino acids chain length, although other substantially equivalent polymer carriers can also be used. It is desirable for the final antibody conjugate to be soluble in human serum, for ease of administration and efficient targeting, when used as an in vivo diagnostic or therpeutic agent. Thus, solubilizing functions on the carrier polymer will enhance the serum solubility of the final conjugate. In particular, an aminodextran with hydroxyl functions on the amine portion will be preferred.

The process for preparing a conjugate with an aminodextran carrier normally starts with a dextran polymer, advantageously a dextran of average molecular weight (MW) of about 10,000–100,000, preferably about 30,000–60,000, and more preferably about 40,000. The dextran is then reacted with an oxidizing agent to effect a controlled oxidation of a portion of its carbohydrate rings to generate aldehyde groups. The oxidation is conveniently effected with glycolytic chemical reagents, e.g., $NaIO_4$, according to conventional procedures.

It is convenient to adjust the amount of oxidizing agent so that about 50–150, preferably about 100 aldehyde groups are generated, for a dextran of MW of about 40,000, with about the same proportion of aldehyde groups for other MW dextrans. A larger number of aldehyde groups, and subsequent amine groups, is less advantageous because the polymer then behaves more like polylysine. A lower number results in less than desirable loading of drug, toxin, chelator, boron addend or label molecules, which may be disadvantageous.

The oxidized dextran is then reacted with a polyamine, preferably a diamine, and more preferably a mono- or polyhydroxy diamine. Suitable such amines include, e.g., ethylene diamine, propylene diamine or other like polymethylene diamine, diethylene triamine or like polyamines, 1,3-diamino-2-hydroxypropane or other like hydroxylated diamine or polyamine, and the like. Earlier workers have generally used ethylene diamine, but the present inventors have shown that better results are achieved with a solubilizing diamine such as 1,3-diamino-2-hydroxypropane. An excess of the amine relative to the aldehyde groups is used, to insure substantially complete conversion of the aldehyde functions to Schiff base (imine) groups.

Reductive stabilization of the resultant intermediate is effected by reacting the Schiff base intermediate with a reducing agent. e.g., $NaBH_4$, $NaBH_3CN$ or the like. An excess of the reducing agent is used to assure substantially complete reduction of the imine groups to secondary amine groups, and reduction of any unreacted aldehyde groups to hydroxyl groups. The resultant adduct can be further purified by pasage through a convential sizing column to remove cross-linked dextrans. An estimate of the number of available primary amino groups on the AD can be effected by reaction of a weighed sample with trinitrobenzenesulfonic acid and correlation of the optical density at 420 nm with a standard. This method normally results in essentially complete conversion of the calculated number of aldehyde groups to primary amine groups on the AD.

Other conventional methods of derivatizing a dextran to introduce amine functions can also be used, e.g., reaction with cyanogen bromide, followed by reaction with a diamine.

The AD is then reacted with a derivative of the particular drug, toxin, chelator, boron addend or label to be loaded, in an activated form, preferably a carboxyl-activated derivative, prepared by conventional means, e.g., using dicyclohexylcarbodiimide (DCC) or a water soluble varient thereof, to form an intermediate adduct.

Methotrexate (MTX) is a typical drug for use in preparing conjugates according to the invention and will be used to illustrate the procedure. Analogous steps will be used for other drugs, toxins, chelators, boron addends and labels, modified in appropriate ways which will be readily apparent to the ordinary skilled artisan. Activation of MTX is conveniently effected with any of the conventional carboxyl-activating reagents, e.g., DCC, optionally followed by reaction with N-hydroxysuccinimide (HOSu), to form the active ester. The reaction is normally effected in a polar, aprotic solvent, e.g., dimethylformamide (DMF), dimethylsulfoxide (DMSO) or the like. Other activated esters, e.g., p-nitrobenzoate and the like, can also be used, as can mixed anhydrides. The DCC/HOSu activation is mild and the activated MTX can be reacted in aqueous medium with the AD, so it is preferred.

The proportions of activated MTX to AD are preferably such that about half of the amino groups available on the AD react to form amide bonds with the carboxyl of the activated MTX. Thus, if about 100 amine groups are available on an AD with a starting MW of about 40,000, up to about 50 of these should be reacted with activated MTX. Using a proportion of about 50:1 MTX:AD, about 25-50 MTX molecules are normally introduced. It is difficult to achieve higher loading because of incipient precipitation of the adduct due to the increasing insolubility thereof.

As an illustration of the adaptations to be used for other drugs, loading with 5-flourouracil (5-FU) can be effected by oxidizing 5-flourouridine at the carbohydrate, e.g., using periodate, reacting this intermediate with an aminodextran, and reductively stabilizing the Schiff base adduct. Cycloheximide can be loaded by direct reaction of its cyclohexanone carbonyl with aminodextran amine groups, followed by reductive stabilization, or by reacting its side chain hydroxyl with an excess of a diisothiocyanate linker and reaction of the isothiocyanate derivative with amines on the aminodextran, or by reaction of the imide nitrogen with, e.g., a haloacid or haloester, followed by activation of the resultant carboxyl derivative, e.g., with DCC, and condensation with amines on the aminodextran.

Another illustration is provided by the antibiotic mitomycin C and its analogues. This molecule has an amine function and a cyclic imine, either of which can be reacted with an alkylating activating group, e.g., succinimidyloxy iodoacetate or sulfosuccinimidyloxy (4-iodoacetyl)aminobenzoate (sulfo-SIAB), the resulting intermediate is then used to alkylate amine groups on an aminodextran. Alternatively, carboxyl groups can be introduced using, e.g., succinic anhydride, then activated, e.g., with DCC, and the activated intermediate coupled as before.

Toxins, e.g., pokeweed antiviral protein (PAP) or the ricin A-chain, and the like, can be coupled to aminodextrans by glutaraldehyde condensation or by reaction of activated carboxyl groups on the protein with amines on the aminodextran.

A polypeptide carrier can be used instead of an AD, but it must have at least 50 amino acids in the chain, preferably 100-5000 amino acids. At least some of these amino acids should be lysine residues or glutamate or aspartate residues with pendant carboxylates. The pendant amines of lysine residues and the pendant carboxyls of glutamate and aspartate are convenient for attaching drug, toxin, chelator, boron addend or label molecules to the polymer. Examples of suitable such PP's include, e.g., polylysine, polyglutamic acid, polyaspartic acid, copolymers thereof, and mixed polymers of these amino acids and others, e.g. serines, to confer desirable solubility properties on the resultant loaded carrier and antibody conjugate.

Many drugs and toxins are known which have a cytotoxic effect on tumor cells or microorganisms that may infect a human and cause a lesion, in addition to the specific illustrations given above. They are to be found in compendia of drugs and toxins, such as the Merck Index and the like. Any such drug can be loaded onto the AD or PP by conventional means well known in the art, and illustrated by analogy to those described above.

Chelators for radiometals or magnetic resonance enhancers are also well known in the art. Typical are derivatives of ethylenediaminetetraacetic acid (EDTA) and diethylenetriaminepentaacetic acid (DTPA). These typically have groups on the side chain by which the chelator can be attached to a carrier. Such groups include, e.g., a benzylisothiocyanate, by which the DTPA or EDTA can be coupled to the amine group of an antibody. In the present invention, this same group would be used to couple the chelator to amine groups on an AD or PP. Alternatively, carboxyl groups or amine groups on a chelator can be coupled to an AD or a PP by activation or prior derivatization and then coupling, all by well known means. For example, deferoxamine, which is a chelator for Ga-67, has a free amine group that can be coupled to an activated carboxyl of a PP containing glutarate or aspartate residues, or can be activated with a suitable linker to contain an activated carboxyl, isothiocyanate or like group, and then coupled to amines on an AD or a PP with lysine residues therein.

Other methods of linking chelators to amines of an AD will be apparent to the skilled artisan, depending upon the functionality of the chelator. Such linkages to amine or carboxyl groups of antibodies is known, and can be adapted readily to linkage to AD or PP carrier polymers. Linkage to other functions on the chelator will also be apparent, e.g., to sulfhydryls by alkylation to form thioethers, to hydroxyls by acylation to preferably form urethanes or to form esters, to aromatic rings by diazonium coupling to a group which can then be further converted to a carboxyl or amine for coupling to carrier.

Labels such as enzymes, fluorescent compounds, electron transfer agents, and the like can also be linked to carrier by conventional methods well known to the art. These labeled carriers and the antibody conjugates prepared from them can be used for immunoassays and for immunohistology, much as the antibody conjugate prepared by direct attachment of the labels to antibody. However, the loading of the conjugates according to the present invention with a plurality of labels can increase the sensitivity of assays or histological procedures, where only a low extent of binding of the antibody to target antigen is achieved.

Boron addends, e.g., carboranes, when attached to antibodies and targeted to lesions, can be activated by thermal neutron irradiation and converted to radioactive atoms which decay by alpha emission to produce highly cytotoxic short-range effects. High loading of boron addends, as well as of magnetic resonance enhancing ions, is of great importance in potentiating their effects. Carboranes can be made with carboxyl functions on pendant side chains, as is well known in the art. Attachment of these carboranes to AD's or PP's by activation of the carboxyl groups and condensation with amines on the carriers enables preparation of useful loaded carriers.

Conjugation of the adduct with the antibody is effected by oxidizing the carbohydrate portion of the antibody and reacting the resultant aldehyde (and ketone) carbonyls with amine groups remaining on the carrier after loading, or introduced thereon after loading, with the drugs, toxins, chelators, boron addends or labels. Typically, for and AD, not all of the amines of the AD are use to load the carrier, and remaining amines condense with the oxidized antibody to form Schiff base adducts, which are then reductively stabilized, normally with a borohydride reducing agent.

For example, the MTX-AD adduct can be conjugated to any antibody which specifically binds to an antigen produced by or associated with a tumor which is responsive to methotrexate therapy. Examples of such antigens are human chorionic gonadotropin (HCG), carcinoembryonic antigen (CEA), alpha-fetoprotein (AFP), breast gross cystic disease protein, breast epithelial cell antigen, and other breast, lung, ovarian, germ cell, brain, lymphoma and leukemia antigens. Antibodies to such antigens can be developed by immunizing a suitable animal host with purified anticancer antigens or tumor or normal organ/tissue extracts and/or cells.

These antigens and/or cells/extracts can also be used in conventional methods of producing hybridomas which produce monoclonal antibodies. Human or primate hybridoma monoclonal antibodies can be produced by a combination of genetic engineering and hybridoma technology.

The next step involves oxidation of the carbohydrate portion of the antibody chosen for the conjugate. This is conveniently effected either chemically, e.g., with $NaIO_4$ or other glycolytic reagent, or enzymatically, e.g., with neuraminidase and galactose oxidase. The latter is a convenient method which is well known for linking amino moieties to antibodies, e.g., as reported by Banjo et al., Int. J. Cancer, 13:151-163, 1974.

The proportion of oxidized antibody and MTX-AD adduct are adjusted so that an average of about 1-3 adducts are linked to the antibody. This will result in a MW for the conjugate of less than about 300,000, which is desirable to promote adequate loading without interfering with cellular uptake and diffusion into solid tumor, and at the same time avoiding or at least mitigating rapid clearance of the conjugate from the blood stream. Attachment of the MTX-AD conjugate to the antibody in a site-specific manner on the carbohydrate portion of the molecule preserves the antibody binding activity, while at the same time permitting a high loading of the drug.

Analogous procedures are used to produce other conjugates according to the invention. Loaded PP carriers preferably have free lysine residues remaining for condensation with the oxidized carbohydrate portion of an antibody. Carboxyls on the carrier can, if necessary, be converted to amines by, e.g., activation with DCC and reaction with an excess of a diamine.

Loading of drugs on the carrier will depend upon the potency of the drug, the afficiency of antibody targeting and the efficacy of the conjugate once it reaches its target. In most cases, it is desirable to load at least 20, preferably 50 and often 100 or more molecules of a drug on a carrier. The ability to partially or completely detoxify a drug as a conjugate according to the invention, while it is in circulation, can reduce systemic side effects of the drug and permit its use when systemic administration of the unconjugated drug would be unacceptable. For example, MTX and cycloheximide often are too toxic when administered systemically. Administration of more molecules of the drug, but conjugated to antibody on a carrier, according to the present invention, permits therapy while mitigating systemic toxicity.

Toxins will often be less heavily loaded than drugs, but it will still be advantageous to load at least 5, preferably 10 and in some cases 20 or more molecules of toxin on a carrier and load at least one carrier chain on the antibody for targeted delivery.

As noted above, it is often highly advantageous to load many molecules of a chelator on a carrier to form a conjugate, especially when the metal ion to be chelated is a paramagnetic ion for magnetic resonance enhancement. In such cases, higher molecular weight carrier polymer chains are preferably used and more than one loaded carrier is condensed to the carbohydrate portion of the antibody. For example, using an AD made from a dextran of average molecular weight of 100,000, preferably an AD prepared with 2-hydroxy-1,3-diaminopropane, and preferably containing about 100-200 amine groups per dextran, about 100 DTPA chelator groups are coupled, using either a conventional cyclic-DTPA procedure or by reaction with excess of another derivative with an activated carboxyl on a side chain or with another reactive acylating group on the side chain, e.g., an isothiocyanate, or with an alkylating function on the side chain, e.g., an alpha-iodobenzyl or an iodoalkyl group. Coupling of several loaded carrier polymer chains, preferably 1.5-4 chains, to the oxidized carbohydrate portion of antibody will permit loading of 150-400 paramagnetic ions on a single antibody after the chelator conjugate is loaded with the metal ions, by conventional means, preferably in metal-free solution and using a transchelation agent.

Administration of antibody conjugates of the invention for in vivo diagnostic and therapeutic applications will be by analogous methods to conjugates of the same or similar drugs, toxins, chelators or boron adducts where the diagnostic or therapeutic principle is directly linked to antibody or a loade carrier is linked by random binding to amine or carboxyl groups on amino acid residues of the antibody in a non-site-specific manner. Such modes of administration are illustrated in references already cited herein for illustrative purposes, and are also found widely in the literature, so that they will be well known to the skilled artisan. More precise dosimetry will be necessary for each agent, again as is well known in the art.

Administration of the MTX-AD-Ab can be effected in a variety of ways depending upon the type and location of the tumor to be treated. For example, administration can be intravenous, intraarterial, intraperitoneal, intrapleural, intrathecal, subcutaneous, by perfusion through a regional catheter, or by direct intralesional injection.

The conjugate will generally be administered as a sterile aqueous solution in phosphate-buffered saline. Dosage units of about 10–200 mg of conjugate will be administered, normally daily for a period of several days. It may be necessary to reduce the dosage and/or use antibodies from other species and/or hypoallergenic antibodies, e.g., hybrid human or primate antibodies, to reduce patient sensitivity.

Intravenous, intraarterial or intrapleural administration is normally used for lung, breast, and leukemic tumors. Intraperitoneal administration is advised for ovarian tumors. Intrathecal administration is advised for brain tumors and leukemia. Subcutaneous administration is advised for Hodgkin's disease, lymphoma and breast carcinoma. Catheter perfusion is useful for metastatic lung, breast or germ cell carcinomas of the liver. Intralesional administration is useful for lung and breast lesions.

The above illustration will show the general methods of administration of conjugates according to the present invention. Conjugates of boron addend-loaded carrier for thermal neutron activation therapy will normally be effected in similar ways, and it will be advantageous to wait until non-targeted conjugate clears before neutron irradiation is performed. Such clearance can be accelerated by use of second antibody, as is known from, e.g., U.S. Pat. No. 4,624,846.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE 1

Preparation of Amino Dextran

One gram of dextran (MW 40,000, Sigma) is partially oxidized by $NaIO_4$ (0.33 g) in aqueous solution to form polyaldehyde dextran. The mixture is stirred in the dark for 1 hr at room temperature. The solution is concentrated by amicon cell (YM10 membrane MWCO=10,000) and purified by Sephadex G-25 column. The material is lyophilized to give 898 mg of white powder (89.8% yield).

The polyaldehyde dextran (800 mg, 0.02 mmole) is dissolved in 80 ml $H_2O$ and then reacted with 1,3-diamino-2-hydroxypropane (200 mg, 2.15 mmole) at room temperature for 24 hours. Sodium borohydride (11.8 mg, 0.311 mmole) is added and reacted at room temperature for 2 hours. The material is membrane filtered through YM-10 and XM-50 to eliminate the small molecules, and at the same time control the molecule weight at the selected ranges.

The level of the amino groups is assayed by TNBS (trinitrobenzene-sulfonic acid) using glucosamine as the reference material. The $NH_2$ level is found to be 100/dextran.

EXAMPLE 2

Preparation of Methotrexate/aminodextran intermediate (a) Activation of Methotrexate In a dried Reacti-vial, 45.4 mg of methotrexate (0.1 mmole, Sigma) in 1 ml anhydrous DMF is introduced by syringe. A solution of N-hydroxysuccinimide (23 mg, 0.2 mmole, Sigma) in 7590 ul of anh. DMF and a solution of 1,3-dicyclohexylcarbodiimide (41.5 mg, 0.2 mmole, Sigma) in 750 ul of anh. DMF are followed. The reaction mixture is stirred in the dark at room temperature for 16 hours under anhydrous conditions. The white precipitate is centrifuged and the clear solution is stored in a sealed bottle at $-20°$ C.

(b) Reaction with Aminodextran

Aminodextran (10 mg, $2.5 \times 10^{-4}$ mmole) is dissolved in 2 ml of PBS, pH 7.2. Activated MTX ($125 \times 10^{-4}$ mmole) is added gradually. The solution is stirred at room temperature for 5 hours and purified by Sephadex G-25 column. The void volume is collected and further dialyzed against reaction buffer. After lyophilization, 2.1 mg of product is obtained (21% yield). The methotrexate incorporation is determined by the absorption at 370 nm ( =6500) to be 38 Methotrexate/dextran.

EXAMPLE 3

Preparation of Antibody Conjugate (a) Oxidation of Antibody

Anti-CEA monoclonal antibody is selectively oxidized by sodium metaperiodate to form aldehyde groups on the carbohydrate moiety. The procedure is as follows: Antibody (2 mg/ml) in PBS, pH 7.2 is reacted with 20 ul of sodium metaperiodate (2.84 ng/ml) in the dark at room temperature for 90 minutes. Ethylene glycol (2 ul) is then added. After 15 minutes, the oxidized antibody is purified by Sephadex G-25 column. The IgG fraction is collected and condensed to approximately 1 ml and used in the following conjugation.

(b) Conjugation

The oxidized antibody (about 2 mg) is reacted with methotrexate/aminodextran intermediate prepared according to Example 2 (2.5 mg, $62.5 \times 10^{-6}$ mmole) in PBS, pH 7.2. The solution is reacted at 4° C. for 48 hours. The resultant Schiff base is stabilized by sodium cyanoborohydride (10-fold excess over the antibody). After sizing chromatography on Sephacryl S-300, the conjugate appears as a symmetrical peak and is collected. The protein concentration is determined by Lowry assay to be 1.05 mg (52.5% yield). The concentration of methotrexate is determined by the absorption at 370 nm (=6500). The conjugate is found to contain 91 molecules of methotrexate per IgG molecule, which indicates that at least two dextran bridges are attached to the antibody.

The immunoreactivity of the conjugate is studied by flow-cytometry using indirect flourescence label technique. The data are compared with unmodified antibody and show that the conjugation by this method does not alter the immunoreactivity of the antibody.

EXAMPLE 4

Preparation of 5-FU Antibody Conjugate

Polylysine of average molecular weight 10,000 is reacted with 5-fluorouridine which has been oxidized with periodate. The condensation product is reductively stabilized with sodium borohydride. The loaded PP has an average of 40 5-FU groups on the polymer. Condensation of the loaded carrier with oxidized antibody, by a similar procedure to that of Example 3, produces a conjugate with 1-3 carrier groups attached.

EXAMPLE 5

Preparation of Chelator Conjugate

An aminodextran of molecular weight 100,000 is reacted with cyclic-DTPA to produce loaded carrier having an average of 100 DTPA groups thereon. Condensation of the resultant loaded carrier with oxidized antibody, followed by reductive stabilization, gives a conjugate with 1-3 carrier groups per antibody, with negligible reduction in immunoreactivity. Loading of the conjugate with gadolinium(III) ions or with Indium-111, Gallium-67 or Technetium-99 m produces highly loaded conjugate for scintigraphic or magnetic resonance imaging. Loading with, e.g., Yttrium-90 produces a therapeutically useful targeting agent.

EXAMPLE 6

Cytotoxicity of MTX Conjugate

LS174T (colon adenocarcinoma) cells are treated with trypsin/EDTA, washed with complete media (RPMI-1640, 10% FCS, 1000 u/ml penicillin, 1000 ug/ml streptomycin, 25 mM Hepes), and added to microtiter well strips at $4 \times 10$ cells/well in 100 ul, 6 replicates for each treatment. After 4 hrs, 37° C., 6% $CO_2$, antibody-methotrexate conjugates are added along with the appropriate controls (free MTX, free MTX+free antibody). The cells are incubated for an additional 24 hours 37° C., 6% $CO_2$, at which time 0.1 uCi of 75-Se-selenomethionine is added for 16-18 hrs. Plates are washed 4 times. Individual wells are separated and counted in a gamma counter. The conjugate at a dose of about 3 uM causes about 50% of cell mortality.

EXAMPLE 7

Tumor Therapy

A female patient having a small-cell carcinoma diffusely metastasized in both lobes of the lung is treated by intravenous injection of a solution of 100 mg of MTX-AD-anti-CEA antibody conjugate in PBS, at a concentration of 10 mg/ml. The treatment is repeated for five successive days. CAT scans prior to treatment and 30 days after the last administration of the conjugate demonstrate 60% reduction in tumor volume.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A soluble antibody conjugate, comprising a plurality of drug, toxin, chelator, boron addend or detectable label molecules covalently bound to a polymer carrier having at least one remaining free amine group, to form a loaded carrier, said loaded carrier in turn being covalently bound through said at least one amine group to the carbohydrate portion of an antibody by a reduced Schiff base linkage; wherein said conjugate is soluble in human serum.

2. The antibody conjugate of claim 1, wherein said antibody is a monoclonal antibody.

3. The antibody conjugate of claim 1, wherein said polymer carrier is an aminodextran or a polypeptide of at least 50 amino acids in length.

4. The antibody conjugate of claim 1, wherein said antibody is an anti-cancer antibody.

5. The antibody conjugate of claim 4, wherein said anti-cancer antibody specifically binds to an antigen produced by or associated with a lung, breast, colorectal, liver, pancreatic, urogenital, stomach, kidney, lymphoid or epidermoid cancer.

6. The antibody conjugate of claim 1, wherein said antibody specifically binds to an antigen produced by or associated with a non-cancerous infectious or inflammatory lesion.

7. The antibody conjugate of claim 1, wherein said antibody specifically binds to a target of a specific type of normal organ or tissue.

8. The antibody conjugate of claim 1, wherein said polymer carrier is an aminodextran.

9. The antibody conjugate of claim 8, wherein said aminodextran is a condensation product of dextran and 1,3-diamino-2-hydroxypropane.

10. The antibody conjugate of claim 8, wherein said aminodextran has about 50-150 amino groups thereon.

11. The antibody conjugate of claim 1, wherein said polymer carrier is a polypeptide chain of at least 50 amino acids in length.

12. The antibody conjugate of claim 1, wherein said polymer carrier is loaded with a plurality of molecules of a cytotoxic agent.

13. The antibody conjugate of claim 12, wherein said cytotoxic agent is an anti-cancer drug.

14. The antibody conjugate of claim 13, wherein said anti-cancer drug is methotrexate, 5-fluorouracil, cycloheximide, daunomycin, doxorubicin, chlorambucil, trenimon, phenylenediamine mustard, adriamycin, bleomycin, cytosine arabinoside or cyclophosphamide.

15. The antibody conjugate of claim 12, wherein said cytotoxic agent is a toxin.

16. The antibody conjugate of claim 15, wherein said toxin is ricin or the A-chain thereof or pokeweed antiviral protein.

17. The antibody conjugate of claim 1, wherein said polymer carrier is loaded with a plurality of molecules of an antibiotic.

18. The antibody conjugate of claim 17, wherein said antibiotic is an antiviral, antifungal or antimicrobial drug.

19. The antibody conjugate of claim 17, wherein said antibiotic is an antineoplastic mitomycin or actinomycin.

20. The antibody conjugate of claim 1, wherein said polymer carrier is loaded with a plurality of molecules of a boron addend.

21. The antibody conjugate of claim 17, wherein said boron addend comprises a carborane.

22. The antibody conjugate of claim 1, wherein said polymer carrier is loaded with a plurality of molecules of a chelator.

23. The antibody conjugate of claim 22, wherein said chelator is a chelator for a radiometal.

24. The antibody conjugate of claim 22, wherein said chelator is a chelator for a magnetic resonance enhancing metal ion.

25. The antibody conjugate of claim 22, wherein said chelator comprises: (a) an ethylenediaminetetraacetic acid or diethylenetriaminepentaacetic acid mostly; (b) deferoxamine; or (c) a bisthiosemicarbazone of a 1,2- or 1,3-dicarbonyl compound.

26. The antibody conjugate of claim 1, wherein said polymer carrier is loaded with a plurality of molecules of a detectable label.

27. The antibody conjugate of claim 26, wherein said label is an enzyme, a fluorescent compound or an electron transfer agent.

28. A method of preparing a soluble antibody conjugate, comprising the steps of:
(a) reacting a polymer carrier, to which are covalently bound a plurality of drug, toxin, chelator, boron addend or detectable label molecules, said carrier having at least one remaining free amine group, with an antibody having an oxidized carbohydrate portion; and
(b) reductively stabilizing the resultant Schiff base adduct;
wherein said conjugate is soluble in human serum.

29. In a scintigraphic imaging agent composition, comprising: (a) a radiolabeled antibody which specifically binds to an antigen produced by or associated with a cancer or other pathological lesion; and (b) a sterile, pharmaceutically acceptable injection vehicle,
the improvement wherein said radiolabeled antibody is the antibody conjugate of claim 23.

30. In a magnetic resonance imaging agent composition, comprising: (a) an antibody labeled with a magnetic resonance enhancing metal ion, wherein said antibody specifically binds to an antigen produced by or associated with a cancer or other pathological lesion; and (b) a sterile, pharmaceutically acceptable injection vehicle,
the improvement wherein said labeled antibody is the antibody conjugate of claim 24.

31. A therapeutic composition for treatment of humans, comprising: (a) the antibody conjugate of any of claims 4, 6, 7, 12, 13, 15, 17, 22, and 23; and (b) a sterile, pharmaceutically acceptable injection vehicle.

32. A diagnostic composition for immunoassay or immunohistology, comprising the antibody conjugate of claim 1, wherein said polymer carrier is loaded with a plurality of molecules of a detectable label.

* * * * *

UNITED STATES PATENT AND TRADEMARK OFFICE
CERTIFICATE OF CORRECTION

| | |
|---|---|
| PATENT NO. | : 5,057,313 |
| DATED | : October 15, 1991 |
| INVENTOR(S) | : Lisa B. Shih et al. |

It is certified that error appears in the above-identified patent and that said Letters Patent is hereby corrected as shown below:

Column 1,
Line 13, please insert:

-- GOVERNMENT LICENSE RIGHTS

The U.S. Government has a paid-up license in this invention and the right in limited circumstances to require the patent owner to license others on reasonable terms as provided for by the awarded by the National Institutes of Health. --

Signed and Sealed this

Twenty-third Day of October, 2001

*Attest:*

*Attesting Officer*

NICHOLAS P. GODICI
*Acting Director of the United States Patent and Trademark Office*